United States Patent
Hayashi et al.

(10) Patent No.: US 6,720,426 B2
(45) Date of Patent: Apr. 13, 2004

(54) PROCESS FOR PRODUCING 2-(4-PYRIDYL) ETHANETHIOL

(75) Inventors: Hideto Hayashi, Yokkaichi (JP); Koichi Hayashi, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/435,375

(22) Filed: May 12, 2003

(65) Prior Publication Data

US 2003/0195112 A1 Oct. 16, 2003

Related U.S. Application Data

(63) Continuation of application No. PCT/JP01/08391, filed on Sep. 26, 2001.

(30) Foreign Application Priority Data

Nov. 21, 2000 (JP) ........................................ 2000-353766
Mar. 27, 2001 (JP) ........................................ 2001-089306

(51) Int. Cl.⁷ ............................................. C07D 213/32
(52) U.S. Cl. ...................................... 546/339
(58) Field of Search .......................................... 546/339

(56) References Cited

FOREIGN PATENT DOCUMENTS

| JP | 11-228540 | 8/1999 |
| JP | 11-255748 | 9/1999 |

OTHER PUBLICATIONS

El Heweihi Zaki, "Notiz über die Identifizierung der Aldosen als deren β–Phenyl–äthyl–mercaptale", *Chemische berichte*, (1953), Jahrg 86, Nr. 6, pp. 781–784.

*Primary Examiner*—Patricia L. Morris
(74) *Attorney, Agent, or Firm*—Oblon, Spivak, McClelland, Maier & Neustadt, P.C.

(57) ABSTRACT

An object of the present invention is to provide a process for producing 2-(4-pyridyl)ethanethiol easily.

According to the invention, 4-vinylpyridine is reacted with thiourea in an aqueous medium containing an acid to form a solution containing an isothiuronium salt and then the solution is made alkaline to convert the isothiuronium salt into 2-(4-pyridyl)ethanethiol.

6 Claims, No Drawings

PROCESS FOR PRODUCING 2-(4-PYRIDYL) ETHANETHIOL

TECHNICAL FIELD

The present invention relates to an improvement of a process for producing 2-(4-pyridyl)ethanethiol from 4-vinylpyridine and thiourea. 2-(4-Pyridyl)ethanethiol is a useful compound as an synthetic intermediate for medicaments and pesticides and also is a useful compound as a modifying agent for catalysts at the production of bisphenol A by condensing phenol and acetone.

BACKGROUND ART

Although a large number of reports have been hitherto published on the synthesis of pyridylalkylthiols, with regard to the synthesis of 2-(4-pyridyl)ethanethiol, a method of reacting 4-vinylpyridine with thiourea in the presence of p-toluenesulfonic acid in an ethanol solvent to form an isothiuronium salt and then converting it into 2-(4-pyridyl) ethanethiol in ammonia water is considered to be practical, which is described in Journal of Organic Chemistry (J. Org. Chem.), 26, 82 (1961), and an improvement of this method has been advanced (cf. Japanese Patent Laid-Open Nos. 228540/1999 and 255748/1999).

One problem in the process of reacting 4-vinylpyridine with thiourea in ethanol is the necessity of providing a reaction apparatus with a strong stirring means because the reaction solution becomes slurry owing to precipitation of the isothiuronium salt formed during the reaction. The other problem is that the isothiuronium salt should be recovered by solid-liquid separation from the reaction solution, washed, dried, and then converted into 2-(4-pyridyl) ethanethiol with ammonia water as the next step, and the operations are tedious and complex and take a long period of time. Furthermore, since an alcoholic organic solvent such as ethanol is used as a reaction solvent, a large quantity of organic waste is generated, which results in a large load on the environment.

Accordingly, it is an object of the invention to provide a process for producing 2-(4-pyridyl)ethanethiol which is free from such problems.

DISCLOSURE OF THE INVENTION

Paying attention to the fact that the isothiuronium salt as an intermediate of the reaction is water-soluble, the present inventors have found that 2-(4-pyridyl)ethanethiol can be produced by reacting 4-vinylpyridine with thiourea in an aqueous medium in a yield equal to that in the reaction in ethanol, without isolating or purifying the isothiuronium salt on the way.

Namely, according to the present invention, 2-(4-pyridyl) ethanethiol can be produced in simple operations and in good yields by reacting 4-vinylpyridine with thiourea in an aqueous medium containing an acid to form a solution containing an isothiuronium salt and then making the solution alkaline to convert the isothiuronium salt into 2-(4-pyridyl)ethanethiol. Moreover, since an aqueous medium is used as a reaction medium, organic waste can be reduced.

BEST MODE FOR CARRYING OUT THE INVENTION

According to the present invention, 4-vinylpyridine is reacted with thiourea in an aqueous medium in the presence of an acid to form an isothiuronium salt. The reaction proceeds as follows.

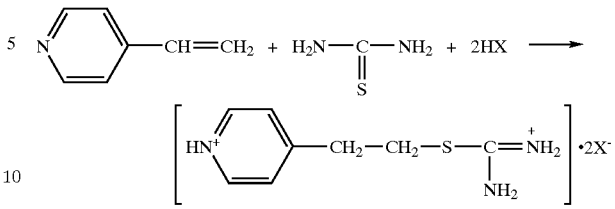

As the acid, use may be made of organic acids such as p-toluenesulfonic acid, benzenesulfonic acid, and trifluoromethanesulfonic acid and general inorganic acids such as sulfuric acid, hydrochloric acid, and nitric acid. Preferably, aromatic sulfonic acids such as p-toluenesulfonic acid and benzenesulfonic acid and sulfuric acid which are easy to handle are used. Of these, p-toluenesulfonic acid or sulfuric acid is preferably used.

The acid is used in such an amount that may be a stoichiometric amount shown in the above scheme or more based on 4-vinylpyridine, but since the use of an excess amount of the acid may induce a side reaction, the acid is preferably used in an amount of 4 equivalents or less, particularly 3 equivalents or less based on 4-vinylpyridine. In this connection, a higher concentration of the acid in the aqueous medium is preferable unless the easiness of the reaction operations is impaired, and in the case of p-toluenesulfonic acid, the concentration is preferably from about 5 to 50% by weight, particularly about 20 to 40% by weight.

Moreover, thiourea is used in a stoichiometric amount or an amount slightly more than the amount, and it is preferable to use it in an amount of 1.5 equivalents or less, particularly 1.3 equivalents or less.

The reaction may be effected by dissolving an acid and thiourea into an aqueous medium and then adding dropwise 4-vinylpyridine thereto under stirring. The reaction may be carried out preferably at an elevated temperature of 30 to 100° C., particularly 50 to 100° C. for 1 to 10 hours under an inert gas atmosphere such as nitrogen.

When the reaction of forming the isothiuronium salt is completed, the reaction solution is cooled to 50° C. or lower and the solution is made alkaline by adding an alkali to convert the isothiuronium salt into 2-(4-pyridyl)ethanethiol. As the alkali, sodium hydroxide and the like may be used but ammonia is preferably used. When ammonia is used, the reaction proceeds as follows.

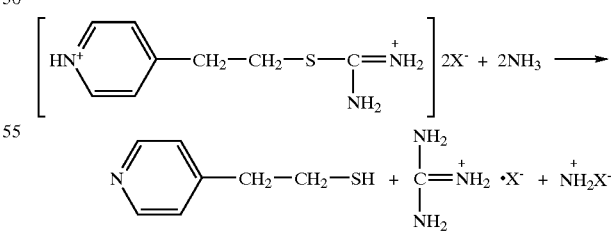

Although a stoichiometric amount of required ammonia is two molar equivalents relative to the isothiuronium salt, but it is preferable to use an excess amount of ammonia, usually three molar equivalents or more relative to the isothiuronium salt for complete proceeding of the reaction. In this connection, since the acid used excessively in the previous step is also present in the isothiuronium salt solution, in addition to the amount required for neutralizing the acid, it is preferable to use ammonia in an amount of 3 to 15 molar equivalents, particularly 3 to 5 molar equivalents relative to 4-vinylpyridine used as a starting material. When the amount of ammonia is too large, the yield generally decreases. This is probably because 2-(4-pyridyl)ethanethiol formed causes a side reaction. Ammonia is usually used as ammonia water which is easy to handle, and the concentration may be determined in consideration of operability at following filtration and extraction steps.

The conversion of the isothiuronium salt into 2-(4-pyridyl)ethanethiol is completed under stirring at 30 to 70° C. for about 0.5 to 10 hours. However, since the yield tends to decrease by the occurrence of a side reaction when a solution temperature is high at the addition of an alkali, it is preferable to maintain the solution at a temperature of 50° C. or lower at the time when an alkali is added. However, when the solution temperature is low, the reaction rate of the conversion decreases. In order to avoid the decrease of the yield and accelerate the conversion, it is preferable that the solution is maintained at a temperature of less than 50° C. at least until the solution reaches a neutral point and then warmed to a temperature of 50° C. or higher.

After completion of the reaction, in the case that an aromatic sulfonic acid is used as the acid, the reaction product solution is cooled to about 10° C. to precipitate a guanidinium salt formed as a by-product and an extraction solvent such as chloroform is further added thereto, followed by filtration to remove insoluble matter. The residue is further washed with the extraction solvent and the washing liquid is combined with the filtrate. Then, the filtrate is subjected to liquid separation and an extraction solvent phase is recovered. In the case that an inorganic acid such as sulfuric acid is used as the acid, no guanidinium salt precipitates by cooling and hence, in this case, a direct extraction operation with an organic solvent may be carried out without filtration.

In both cases, the aqueous phase is further extracted with an extraction solvent and the resulting extraction solvent phase is combined with the previously obtained extraction solvent phase. After removal of the extraction solvent therefrom, objective 2-(4-pyridyl)ethanethiol can be obtained by distilling the residual liquid under reduced pressure.

EXAMPLES

The following will explain the invention in more detail with reference to Examples but the invention is not limited to the following Examples unless it exceeds the gist.

Example 1

To a 100 ml-volume four-neck flask equipped with a thermometer, a Dimroth condenser and a dropping funnel were charged 15.76 g (0.0828 mol) of p-toluenesulfonic acid monohydrate (mfd. by Kishida Chemical Co., Ltd.), 3.00 g (0.0395 mol) of thiourea (mfd. by Wako Pure Chemical Industries, Ltd.) and 30 ml of water, and they were dissolved each other. The whole was heated to 70° C. under a nitrogen atmosphere and, under maintaining the temperature, 4.13 g (0.0392 mol) of 4-vinylpyridine (mfd. by Tokyo Kasei K.K.) was added dropwise thereto over a period of about 30 minutes. Subsequently, the mixture was warmed to 80° C. and reacted for 3 hours at the temperature.

After completion of the reaction, the reaction product solution was cooled to 20° C. No solid precipitated. To the reaction product solution was added dropwise 12.41 g (0.229 mol as ammonia) of 28% ammonia water over a period of about 30 minutes with attention paid to heat generation. Then, the whole was warmed to 60° C. and reacted at the temperature for 1 hour. The mixture was cooled to 5° C. and 10 ml of chloroform was added thereto, followed by removal of solids by filtration. Operations of subjecting the filtrate to liquid separation and extracting the aqueous phase after 10 ml of chloroform was added thereto were performed four times. When all the chloroform phases were combined and part thereof was analyzed by means of gas chromatograph, the yield of 2-(4-pyridyl)ethanethiol was found to be 4.42 g (0.0317 mol). The percent yield based on 4-vinylpyridine was 80.9% at that time. After chloroform was removed by evaporation under reduced pressure from the chloroform solution, the residual liquid was distilled under reduced pressure to obtain 3.84 g (0.0275 mol) at a boiling point of 87 to 88° C./2.2 mmHg. The percent yield based on 4-vinylpyridine was 70.3%.

Example 2

To a 200 ml-volume four-neck flask equipped with a thermometer, a Dimroth condenser and a dropping funnel were charged 6.00 g (0.0789 mol) of thiourea and 19.2 ml of water. Under a nitrogen atmosphere, 17.1 g of 95% sulfuric acid was added dropwise thereto over a period of about 30 minutes under maintaining the inner temperature at room temperature. After completion of the dropwise addition, the whole was heated to 60° C. and, under maintaining the temperature, 8.38 g (0.0789 mol) of 4-vinylpyridine was added dropwise thereto over a period of about 30 minutes with attention paid to heat generation. Subsequently, the mixture was reacted at 60° C. for 3 hours.

After completion of the reaction, the reaction product solution was cooled to 20° C. and hold for 1 hour. To the reaction product solution was added 48.0 g (0.395 mol as ammonia) of 14% ammonia water with attention paid to heat generation. After completion of the dropwise addition, the reaction solution was warmed to 60° C. and was reacted for 1 hour. When the solution was reacted for a predetermined period of time and then allowed to cool to room temperature, the reaction solution separated into two layers (upper layer: 2-(4-pyridyl)ethanethiol, lower layer: water) but no crystal appeared. The liquid was subjected to liquid separation and the upper layer was collected. Furthermore, the aqueous layer was extracted three times with each of 20 g of toluene. When the combined solution of the resulting extracted solution and the upper layer solution was analyzed by means of gas chromatograph, the yield of 2-(4-pyridyl)ethanethiol was 8.74 g (0.0628 mol). The percent yield based on 4-vinylpyridine was 79.6%.

Example 3

In the same manner as in Example 1, thiourea was reacted with 4-vinylpyridine in an aqueous solution containing p-toluenesulfonic acid. After the reaction product solution was cooled to 40° C., 12.41 g (0.229 mol as ammonia) of 28% ammonia water was added dropwise thereto under maintaining the solution temperature at 40 to 42° C. over a period of about 30 minutes and then the whole was warmed to 60° C. and reacted at the temperature for 1 hour. Thereafter, the mixture was extracted with chloroform in the same manner as in Example 1. When the resulting chloroform phase was analyzed, the yield of 2-(4-pyridyl)ethanethiol was 4.32 g (0.0310 mol) and the percent yield based on 4-vinylpyridine was 79.1%.

Example 4

In the same manner as in Example 1, thiourea was reacted with 4-vinylpyridine in an aqueous solution containing p-toluenesulfonic acid. After the reaction product solution was cooled to 60° C., 12.41 g (0.229 mol as ammonia) of 28% ammonia water was added dropwise thereto under maintaining the solution temperature at 60 to 63° C. over a period of about 30 minutes and further reacted at the temperature for 1 hour. Thereafter, the mixture was extracted with chloroform in the same manner as in Example 1. When the resulting chloroform phase was analyzed, the yield of 2-(4-pyridyl)ethanethiol was 2.69 g (0.0193 mol) and the percent yield based on 4-vinylpyridine was 49.3%.

Comparative Example 1

In accordance with the description in J. Org. Chem., 26, 82 (1961), 2-(4-pyridyl)ethanethiol was produced from 4-vinylpyridine and thiourea.

To a 200 ml-volume four-neck flask equipped with a thermometer, a Dimroth condenser and a dropping funnel were charged 20.9 g (0.11 mol) of p-toluenesulfonic acid monohydrate, 3.8 g (0.05 mol) of thiourea, and 50 ml of ethanol. Under a nitrogen atmosphere, p-toluenesulfonic acid and thiourea were dissolved under stirring by elevating the temperature. Subsequently, the temperature was elevated to 70° C. and, under maintaining the temperature, 5.25 g (0.05 mol) of 4-vinylpyridine was added dropwise over a period of about 30 minutes. After the resulting mixture was reacted under reflux for 3 hours, the reaction product solution was cooled to 5° C. The thus formed isothiuronium salt was recovered by filtration and washed with 30 ml of ether at room temperature and 60 ml of a mixed solution of ether/ethanol (1:1), successively, followed by drying under reduced pressure. The yield of the isothiuronium salt was 23.5 g (0.045 mol) and the percent yield was 89.6%

The above isothiuronium salt was added to a mixed solution of 12.2 g (0.179 mol as ammonia) of 25% ammonia water and 18.3 ml of water and dissolved therein, followed by reaction at 60° C. for 30 minutes. After cooling, 12.1 ml of chloroform was added and solids were removed by filtration. Operations of subjecting the filtrate to liquid separation and extracting the aqueous phase after 10 ml of chloroform was added thereto were performed eight times. All the chloroform phases were combined and chloroform was removed by evaporation under reduced pressure, followed by distillation of the residual liquid under reduced pressure. 4.5 g (0.032 mol) of 2-(4-pyridyl)ethanethiol was obtained at a boiling point of 87 to 88° C./2.2 mmHg. The percent yield based on 4-vinylpyridine was 64%, which almost coincided with the value of 64.8% described in the literature.

Comparative Example 2

To a 500 ml-volume four-neck flask equipped with a thermometer, a Dimroth condenser and a dropping funnel were charged 119.8 g (0.63 mol) of p-toluenesulfonic acid monohydrate, 22.8 g (0.30 mol) of thiourea, and 336 ml of 2-propanol. Under a nitrogen atmosphere, the whole was warmed to 70° C. and 31.5 g (0.30 mol) of 4-vinylpyridine was added dropwise thereto over a period of about 30 minutes with attention paid to heat generation. During the dropwise addition, crystals formed in the reaction solution. After the dropwise addition, the mixture was reacted under reflux for 3 hours and then the reaction product solution was cooled to 5° C. The precipitated isothiuronium salt was recovered by filtration and washed twice with each of 65 ml of 2-propanol to remove excess p-toluenesulfonic acid. The thus obtained salt was dried under reduced pressure to obtain 148.6 g (0.283 mol) of the isothiuronium salt. The percent yield was 94.2%.

Into a mixed solution of 22.31 g (0.367 mol as ammonia) of 28% ammonia water and 33.7 ml of water was dissolved 34.7 g (0.066 mol) of the isothiuronium salt, followed by reaction at 60° C. for 1 hour. After cooling, 20 ml of toluene was added and the formed salt was separated and removed by filtration. The filtrate forming two layers was subjected to liquid separation and the aqueous phase was repeatedly extracted five times with each of 20 ml of toluene. When all the toluene phases were combined and the solution was analyzed on gas chromatograph, the yield of 2-(4-pyridyl) ethanethiol was 7.51 g (0.054 mol). The percent yield based on 4-vinylpyridine was 76.9%.

[Evaluation of Results]

The following points are found from the comparison between the above Examples and Comparative Examples.

(1) Since the isothiuronium salt precipitates in Comparative Examples, operations for separation and washing thereof are required, but in Examples, the salt exists in a dissolved state and thus can be used as it is at next decomposition step.

(2) Since ethanol or isopropanol is used as a reaction medium in Comparative Examples, these solvents becomes organic waste after the reaction but the reaction is carried out in an aqueous system in Examples and hence the system affords no organic waste.

While the invention has been described in detail and with reference to specific embodiments thereof, it will be apparent to one skilled in the art that various changes and modifications can be made therein without departing from the spirit and scope thereof.

The present application is based on Japanese Patent Application filed on Nov. 21, 2000 (Japanese Patent Application No. 2000-353766) and Japanese Patent Application filed on Mar. 27, 2001 (Japanese Patent Application No. 2001-089306), the contents being hereby incorporated by reference.

INDUSTRIAL APPLICABILITY

According to the invention, a process for producing 2-(4-pyridyl)ethanethiol is provided, which is simple in operation and results in a little organic waste. Particularly, 2-(4-pyridyl)ethanethiol can be formed in high yields with suppressing a side reaction by adding an alkali at a low temperature at the time when an isothiuronium salt is converted into 2-(4-pyridyl)ethanethiol by adding an alkali to a solution containing the isothiuronium salt.

What is claimed is:

1. A process for producing 2-(4-pyridyl)ethanethiol comprising a step of reacting 4-vinylpyridine with thiourea in an aqueous medium containing an acid to form a solution containing an isothiuronium salt and a successive step of making the solution alkaline to convert the isothiuronium salt into 2-(4-pyridyl)ethanethiol.

2. The process for producing 2-(4-pyridyl)ethanethiol according to claim 1, wherein the acid is p-toluenesulfonic acid.

3. The process for producing 2-(4-pyridyl)ethanethiol according to claim 1, wherein the acid is sulfuric acid.

4. The process for producing 2-(4-pyridyl)ethanethiol according to claim 1, wherein the solution containing an isothiuronium salt is made alkaline by adding ammonia water to the solution.

5. The process for producing 2-(4-pyridyl)ethanethiol according to claim 1, wherein the solution containing an isothiuronium salt is maintained at a temperature of 50° C. or lower at the time when the solution is made alkaline.

6. The process for producing 2-(4-pyridyl)ethanethiol according to claim 1, wherein the solution containing an isothiuronium salt is maintained at a temperature of less than 50° C. at least until the solution reaches a neutral point and then warmed to a temperature of 50° C. or higher at the time when the solution is made alkaline.

* * * * *